United States Patent [19]
Weigl

[11] 3,961,624
[45] June 8, 1976

[54] METHOD OF DETERMINING LUNG PRESSURE OF A PATIENT USING A POSITIVE PRESSURE BREATHING SYSTEM

[75] Inventor: James Weigl, Santa Monica, Calif.

[73] Assignee: Puritan-Bennett Corporation, Los Angeles, Calif.

[22] Filed: Aug. 9, 1974

[21] Appl. No.: 496,278

Related U.S. Application Data

[62] Division of Ser. No. 313,978, Dec. 11, 1972, Pat. No. 3,871,371.

[52] U.S. Cl. ............................ 128/2.08; 128/145.8
[51] Int. Cl.² ............................................ A61B 5/08
[58] Field of Search .............. 128/2.08, 145.5–145.8

[56] References Cited
UNITED STATES PATENTS

| 3,410,264 | 11/1968 | Frederik | 128/2.08 X |
|---|---|---|---|
| 3,621,835 | 11/1971 | Suzuki et al. | 128/2.08 |
| 3,756,229 | 9/1973 | Ollivier | 128/145.8 |
| 3,848,591 | 11/1974 | Smythe et al. | 128/2.08 X |

FOREIGN PATENTS OR APPLICATIONS

| 1,508,303 | 11/1967 | France | 128/2.08 |

OTHER PUBLICATIONS

*Journ. of Assoc. For Advanc. of Med. Instr.*, vol. 6, No. 1, Jan.–Feb., 1972, pp. 65–69.

Primary Examiner—Kyle L. Howell
Attorney, Agent, or Firm—Fulwider, Patton, Rieber, Lee & Utecht

[57] ABSTRACT

A method for determining the maximum and minimum lung pressure during the breathing cycle of a patient undergoing positive pressure breathing therapy by utilizing a respiration system which includes a console with a gas supply and control unit located at a substantial distance from the patient, and a transfer unit in proximity to the patient. The delivery hose from the transfer unit to the patient is very short and of relatively small volume, so that a pressure sensor located in the transfer unit can monitor the system pressure at a point which has a relatively low volume spacial separation from the patient's lungs. In accordance with the method, a pressure versus time characteristic is generated from the sensed pressure, and the maximum and minimum lung pressures during each breathing cycle are determined from the characteristic by the pressure ordinates of readily identifiable discontinuities in the slope of the characteristic, the discontinuities being reliably indicative of the maximum and minimum lung pressures.

4 Claims, 3 Drawing Figures

METHOD OF DETERMINING LUNG PRESSURE OF A PATIENT USING A POSITIVE PRESSURE BREATHING SYSTEM

This is a division of application Ser. No. 313,978, filed Dec. 11, 1972, now issued as U.S. Pat. No. 3,871,371.

BACKGROUND OF THE INVENTION

This invention resides in the field of respiration systems and controls therefor, and is especially adapted for use with volume-limited ventilators in which a measured volume of gas is delivered to a patient during each inhalation phase of a positive pressure breathing system. It is more particularly directed to a method for reliably ascertaining maximum and minimum lung pressure during each breathing cycle.

Respiration apparatus for positive pressure breathing therapy is in common use, and it has been the usual practive to determine the volume of gas delivery and to control it in accordance with measurements made at the respiration machine. However, the total compliance of the system is a significant factor and one that does not remain constant at all times. Thus, the volume of gas actually delivered to the patient may vary relative to the desired or selected amount.

The effectiveness of patient ventilation depends on an exchange of ample tidal volume of gas in the lungs during each breathing cycle. This is related to the difference between minimum and maximum pressure in the lungs, the maximum pressure occurring at the end of the inspiration phase and the minimum at or near the end of the expiration phase. Should respiration apparatus be adjusted to cycle at too fast a rate, then the lungs may not have time to force out the gas. This could result in the residual or minimum lung pressure climbing to an unacceptable level. Thus, it is highly desirable from the standpoint of adjusting cycle rate, as well as for diagnostic purposes, to know the maximum and minimum lung pressures.

Many improvements have been made over the years in the use of equipment and correction factors to reduce the variation in volume delivery to a low level, and the results are generally quite satisfactory. However, the tidal volume desired for infants is far less then for adults and may be as low as 5 percent or less of the adult requirements. Consequently, the effects of any variation of the system and of any differences that exist in pressure between system and the lungs are correspondingly magnified. Accordingly, there is a need for a supply and control system which makes it possible to monitor the lung pressure and especially the minimum and maximum pressures during each cycle.

SUMMARY OF THE INVENTION

The method of the present invention provides a simple, convenient and highly practical arrangement for ascertaining the maximum and minimum lung pressure during each breathing cycle.

Generally stated, the system by means of which the method of the invention is presently practiced includes a console of the usual type located at a substantial distance from the patient and provided with a volume generator, sensing and control devices, computing equipment, etc., and a transfer unit which is located in proximity to the patient. The gas supply hose which is connected at its inlet end to the volume generator is quite long and of relatively large cross section so that it contains a relatively large volume of gas. The transfer unit is provided with a cavity having inlet and outlet ports and a control valve in the cavity to block or permit flow. The gas supply hose is connected to the inlet port and a delivery hose is connected to the outlet port.

The delivery hose is very short compared to the gas supply hose and is also of much smaller cross section, so that its total volume or dead space is only a small portion of that of the gas supply hose, and is provided with a short nose tube or like delivery means for application to the patient. Since the control valve in the transfer unit provides the cutoff for gas delivery, it will be apparent that the quantity of actual flow to the patient is accurately regulated. The control valve is remotely actuated by a control unit on the console, which coordinates the action of the volume generator and the control valve in accordance with a predetermined program.

Pressure sensing means is provided at the transfer unit for monitoring system pressure. In accordance with the preferred method of the invention, pressure is continuously monitored and a pressure v. time curve is displayed as on an oscilloscope. Discontinuities occur in such curve substantially at the levels of the minimum or residual lung pressure and at the maximum lung pressure during each breathing cycle. Thus, the method of the invention make it possible to determine reliably this important information.

BRIEF DESCRIPTION OF THE DRAWINGS

Various other advantages and features of novelty will become apparent from the following description taken in conjunction with the accompanying drawings, in which.

DESCRIPTION OF THE PREFERRED EMBODIMENTS

Figure 1:
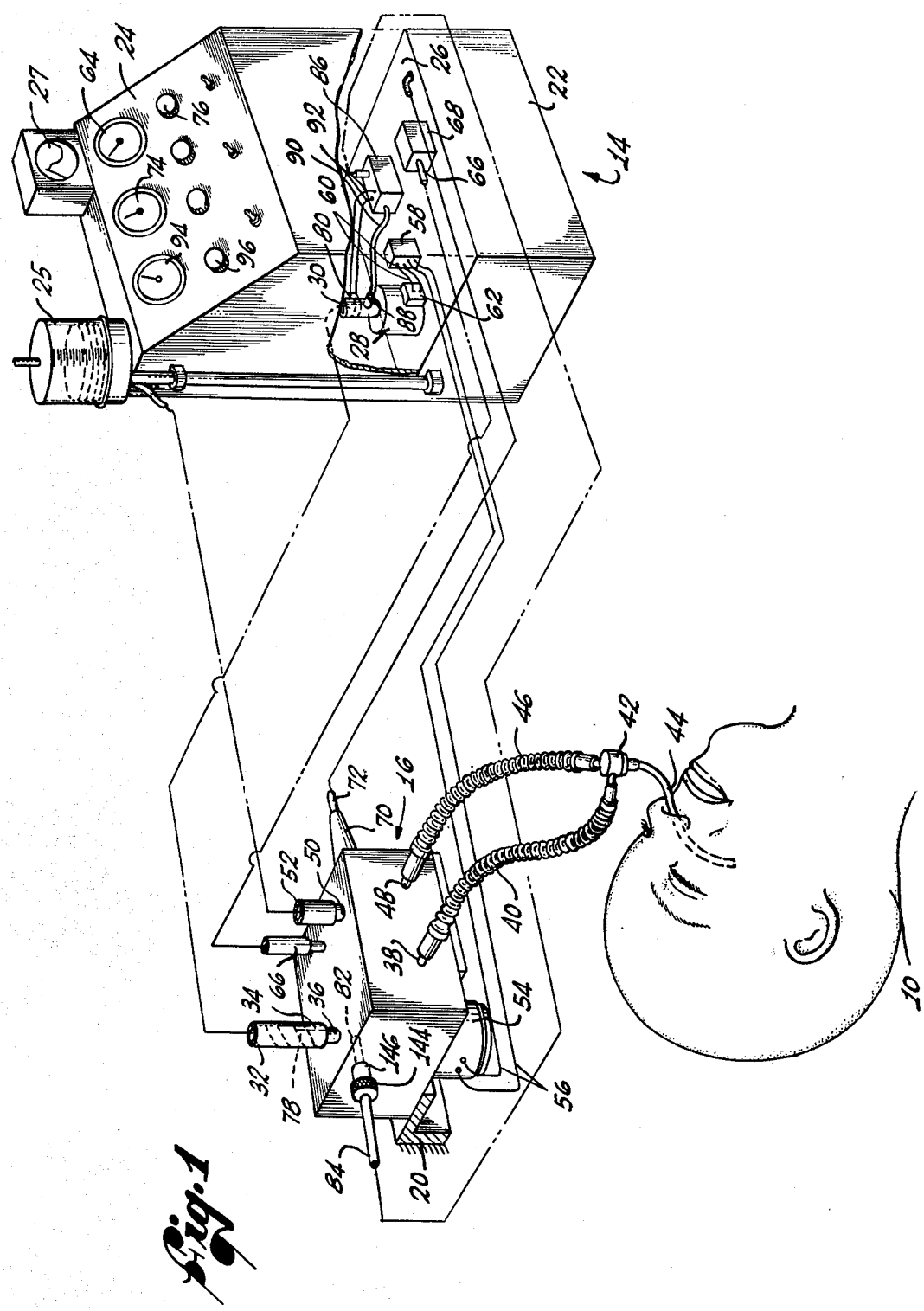
FIG. 1 is a schematic view in perspective of the exemplary apparatus by means of which the method of the invention may be practiced.

A respiration supply and control system by means of which the method of the present invention may be performed is schematically illustrated in FIG. 1, in which a patient 10 is shown lying on a bed or other support at a substantial distance from a console 14 which is provided with various supply and control components. A transfer unit 16 is located in close proximity to the patient and may be mounted by any suitable means or simply positioned on a support 20.

The lower compartment 22 of the console contains various items of computer and automatic control equipment of the type disclosed in application Ser. No. 283,915, entitled COMPLIANCE COMPENSATED VENTILATION SYSTEM, now U.S. Pat. No. 3,834,381, and instrument panel 24 is provided with gauges, manual control knobs and switches. The upper wall of compartment 22 serves as a base 26 to support certain components involved in the operation of the system, and the top of the console supports others including a spirometer 25 and an oscilloscope 27.

A volume generator 28 is mounted on the base 26 and furnishes a desired quantity of a selected breathing gas mixture to the inlet end 30 of a gas supply hose 32, the outlet end 34 of which is connected to a first inlet port 36 on the transfer unit. A supply cavity in the unit is in communication with port 36 and contains an inspiration valve to control flow, and is also connected to a first outlet port 38. A delivery hose 40 is connected to port 38 and extends to a position close to the patient where, in the illustrative case, it is connected to a small manifold 42 from which depends nose tube 44 which is usually installed in one nostril of the patient to deliver gas to the lungs. It will be noted that the delivery hose 40 is very short compared to the length of the gas supply hose 32 and is also much smaller in cross section, so that there is a minimum amount of volume or dead space to affect the actual delivery volume of gas.

The inspiration control valve in the cavity between ports 36 and 38 is actuated by a solenoid 54 which is connected by conductors 56 to control means 58 on the console. This control means is further connected by conductors 60 to the control unit 62 for the volume generator 28, and operates in response to certain programming equipment to actuate the volume generator 28 and the control valve solenoid 54 in planned coordination.

In some cases, a patient may exhale directly to atmosphere, but the system may include a return flow path to the console and to a spirometer, such as Model No. 2642, Monitoring Spirometer, sold by Bennett Respiration Products, Inc. As shown, an expiration hose 46, identical to the hose 40, is connected between manifold 42 and second inlet port 48 on the transfer unit. A second or exhalation cavity in the unit is connected to a second inlet port 48 and to a second exit port 50 and contains a second or exhalation valve to control exhalation flow. A gas return hose 52 is connected to port 50 and extends to the console where it is in flow communication with the spirometer 25. The exhalation valve means is pneumatically actuated and is connected by a conduit 66 to control means 68 which provides pressurized gas to close the valve at a predetermined point in the cycle. A pressure sensor and transducer 70 communicates with the second cavity in the transfer unit and transmits its indications through conductor 72 to the console and thence to the oscilloscope 27. Maximum allowable system pressure may be set by manipulation of a control knob 76.

An additional feature of the system, which is mentioned only in passing, is the control of the temperature of the delivered gas. For this purpose, the hose 32 is provided with a dual winding of a heater filament 78, which may be molded into the hose with both ends terminating at connector 80. A temperature sensor 82 extends into the gas flow path adjacent to port 36 and transmits its indication through conductor 84 to comparatory and temperature controller 86 on the console. A second temperature sensor 88 extends into the gas flow at the inlet end 30 of the hose and transmits its indications through conductor 90 to controller 86. The comparator reads the two indications, and the controller supplies current through conductors 92 to connector 80 and the filament 78 in response to indication of a temperature drop between the inlet and outlet ends of the hose. In this manner, the temperature of the gas may be maintained constant. The temperature indications may also be transmitted to gauge 94, and the operator may adjust the basic temperature by manipulation of a control knob 96.

Figure 2:
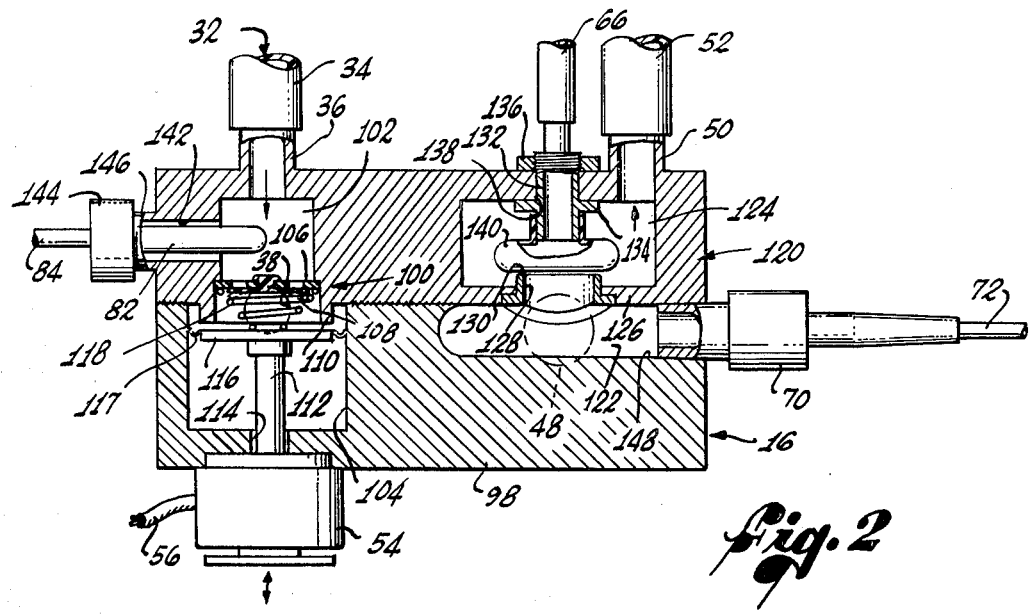
FIG. 2 is a schematic longitudinal sectional view of the transfer unit.

The transfer unit 16 and its various components are schematically illustrated in FIG. 2. The body 98 may take any form but is here shown as a two-piece block solely for purposes of illustration. A first cavity 100 is formed in the body and is preferably circular in cross section. A first end 102 is in flow communication with first inlet port 36 and the second end 104 is in flow communication with first outlet port 38 indicated in phantom lines.

A perforated diaphragm 106 is fixed in the intermediate portion of the cavity and is provided with a flexible leaf type valve head 108 to constitute a check valve which permits flow from the inlet port to the outlet port to supply the patient, but blocks flow in the opposite direction. The second end 104 of the cavity is somewhat larger than the first end and formed to define an annular valve seat 110. The solenoid 54 is fixedly connected to the lower side of body 98 and its armature 112 extends substantially coaxially of the cavity through opening 114 for axial movement. The free end of the armature carries a valve head 116 supported by a flexible diaphragm 117 for sealing purposes and arranged for movement upwards into contact with valve seat 110 to block flow and downward out of contact to permit flow. Tapered coil spring 118 seats on the margin of the diaphragm and contacts head 116 to urge it to open position, while actuation of the solenoid acts to drive it to closed position. The valve 116 thus serves as the first or inspiration control valve.

In operation, with valve 116 open, gas from the volume generator 28 enters port 36 into end 102 of the cavity, readily opens valve 108, and flows into end 104 of the cavity, thence through port 38 and through the delivery hose 40 to the patient. The machine terminates flow and valve 116 is closed to block further flow to the patient. After the machine dumps, valve 116 opens rather quickly, remaining open long enough to permit pressure in the supply hose 32 to be relieved. Even after opening, however, exhalation through hose 40 back through cavity 100 is blocked by the check valve 108.

An opening 142 is formed in the side of body 98 leading into cavity end 102, and temperature sensor 82 extends into the gas stream. A nut 144, engaged with threaded boss 146, retains the sensor in position. As previously mentioned, indications from sensor 82 are transmitted through conductor 84 to the comparator and temperature controller 86 for use in maintaining a constant temperature in the gas supply hose 32.

The body 98 is further provided with a second cavity 120 including a first end 122 in flow communication with second inlet port 48, indicated in phantom lines, and a second end 124 is in flow communication with second outlet port 50. A partition 126 in an intermediate portion of cavity 120 is formed with a central opening 128 having an annular valve seat 130. A fitting 132 having an intermediate flange 134 and an external nut 136 is fixed in place in aperture 138 and its outer end is connected to the conduit 66 which leads to control means 68. A valve head in the form of a hollow flexible body 140 which is generally disk-like is secured on the tubular inner end of the fitting. When pressure fluid is introduced from control means 68 through conduit 66 and fitting 132, body 140 expands axially into contact with valve seat 130 to block flow through the cavity. It thus serves as the second or exhalation control valve. At the proper moment for exhalation purposes, control means 68 relieves the pressure in body 140 to open passage 128, and the exhaled gas flows from the patient through expiration hose 46 and second inlet port 48 through cavity 120, second outlet port 50 and gas return hose 52 to the console where it may flow through the spirometer 25 if desired.

As previously indicated, it is important to know the gas pressure in the lungs during the cycle, especially at the beginning and the end of the inspiratory phase. For this purpose, pressure sensor 70 is mounted in passage 148 which leads into the first end 122 of cavity 120. In this position, it is upstream of valve 140 and thus is in flow communication with the gas in the patient's lungs at all times, even when the inspiration valve is closed. The indications from the pressure sensor 70 are transmitted through conductor 72 to the oscilloscope 27, and the operator may correct values at any time by manipulation of pressure regulator knob 76, or may vary the cycle rate.

Figure 3:
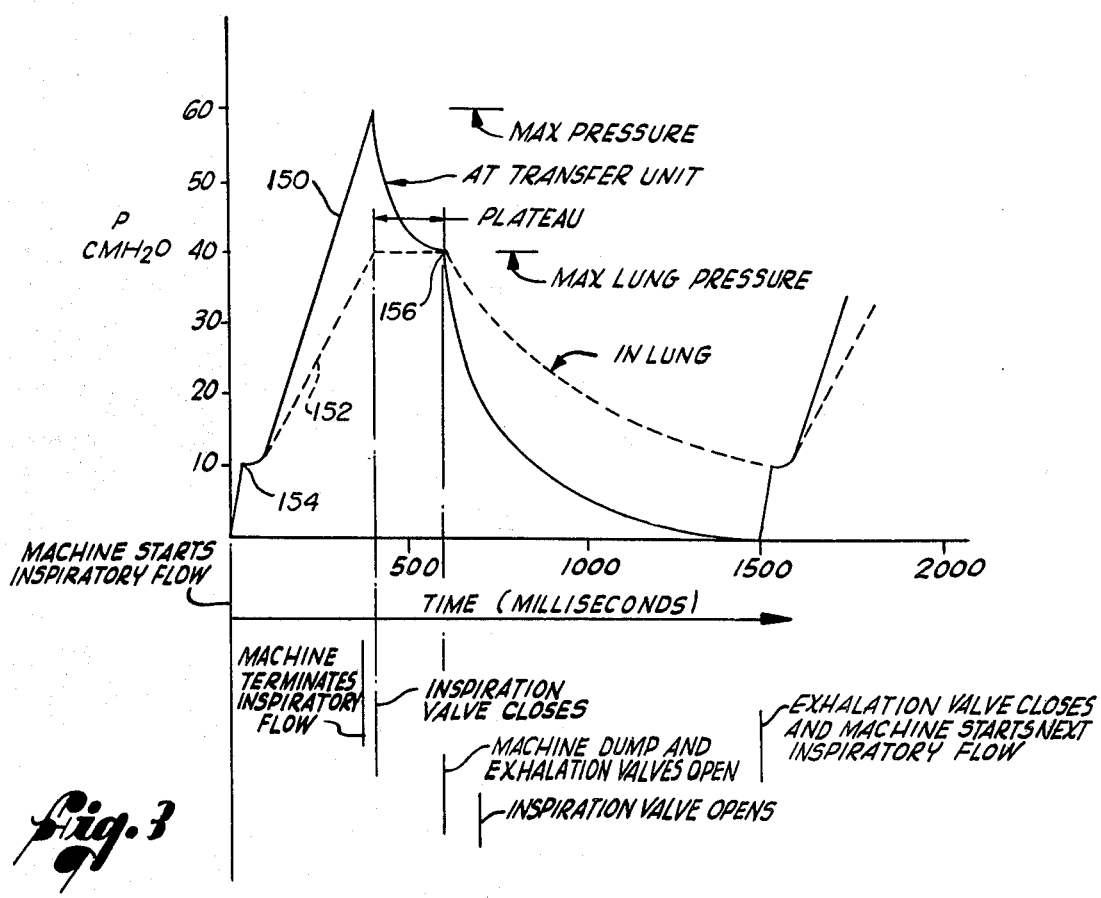
FIG. 3 is a pressure v. time graph illustrating how the maximum and minimum lung pressure values are obtained in accordance with the invention.

The graph of FIG. 3 illustrates the operation of the total system through one complete respiration cycle, including inspiration and expiration phases, to show the interrelation of the various components. These are pressure-time curves with the pressure in centimeters of water and the time in milliseconds based on a breathing rate of 40 cycles per minute, which is typical for treatment of an infant. The line 150 represents pressures at the transfer unit and broken line 152 represents pressures in the lungs. It is, of course, to be understood that the values indicated on the curve are examples of what may be encountered with an infant patient with a restricted lung, and such values are likely to vary considerably from patient to patient.

At the beginning of the cycle, it will be noted that the machine pressure is zero because it has been dumped during the previous cycle, while the residual lung pressure in the illustrative case is assumed to be 10 cm. of water. At this time, the first control valve 116 is open while the second control valve 140 is closed. The system pressure at the transfer unit builds up rapidly to the residual lung pressure (10 cm. $H_2O$) and continues to climb toward its maximum. When the machine control system, after taking the various factors into account, determines that the desired volume of gas has been delivered, inspiratory flow from the machine is terminated. A brief interval later, the length of which corresponds to the response time of the inspiratory valve 116, the latter closes to terminate inspiratory flow to the patient. This is reflected by the peak in a system pressure curve at a maximum pressure of 60 cm. $H_2O$.

The inspiratory phase continues in a holding or plateau portion in which both the inspiration valve 116 and expiration valve 140 are closed, the plateau in this instance being about 200 milliseconds in duration. With the valves in such closed condition, the patient's lungs are in communication with the transfer unit 16 through the relatively small volume, delivery and expiration hoses 40 and 46. Communication to the remainder of the system is blocked by the valves 116 and 140. The combined volume of these hoses and the cavities in the transfer unit 16 is small in relation to the lung volume and, therefore, the system pressure drops off rapidly to the lung pressure. In the illustrative case, the lung pressure and system pressure at the termination of inspiration is approximately 40 cm. $H_2O$.

The exhalation valve 140 opens to commence the exhalation phase and the system pressure sensed by the sensor 70 in the transfer unit rapidly drops off to a zero level. As previously indicated, the exhalation flow is through the path of the hoses 46 and 52 to the spirometer 27. Because of the patient's restricted lung condition, the pressure drop in the lung is much more gradual as reflected by curve line 152. In addition, because of the assumed condition of the patient, the lung pressure only drops to the residual pressure of 10 cm. $H_2O$.

About 100 milliseconds after the start of expiration in the illustrative case, the inspiratory valve 116 again opens so as to provide for intake of air should the patient exert an inspiratory effort prior to the conclusion of the exhalation phase determined by the time cycle rate. It is to be understood that the exhaled gas is still directed to the spirometer 27 because of the presence of check valve 108 in the supply flow path.

As previously noted, the method of the invention makes it possible to monitor the maximum and minimum lung pressure during each breathing cycle. It is highly desirable to have this information available, so that corrective action can be taken, if necessary, by the medical personnel administering the treatment. In the case of the residual or minimum lung pressure, this may involve slowing down the cycle rate to afford a longer time period for the patient to exhale. In the case of the maximum lung pressure, the maximum delivery pressure of the system can be suitably adjusted by control knob 76.

Referring to the curve of FIG. 3, a first discontinuity 154 in the system pressure curve (see line 150) displayed on the oscilloscope 27 occurs substantially at the residual lung pressure and a second discontinuity 156 occurs substantially at the maximum lung pressure. The residual pressure discontinuity 154 in the curve 150 is actually seen as a slight flat in the curve for a brief interval, as well as marking a discernible change in slope. Flow to the transfer unit 16 initially takes place from both the respiration apparatus and back from the patient's lungs. It will be appreciated in this connection that the system pressure of the transfer unit is initially atmospheric or zero, whereas some pressurized gas is still contained in the lungs. Thus, at the very start of inspiration, flow takes place to the transfer unit in both directions, and the rate of pressure increase reflected by the slope of the curve is relatively fast. Once the system pressure builds up to equal that of the residual lung pressure at 10 cm. $H_2O$, the discontinuity 154 occurs, thereby providing a reliable indication of residual lung pressure.

During the remainder of inspiratory flow from the machine, the system pressure build up takes place at a reduced rate reflected by the corresponding portion of the system curve being somewhat flatter than the initial portion. Once inspiratory flow is terminated and the valve 116 closes to commence the "plateau" portion at the end of inspiration, the system curve falls at a rapid rate. As previously explained, this occurs by reason of only a very small volume of gas being trapped in the hoses 40 and 46 between the transfer unit 16 and the patient. Thus, the system pressure sensed by sensor 70 and displayed on the oscilloscope 27 rapidly drops to equal the lung pressure, so that the curve flattens out at the end or produces the second discontinuity 156 seen on the oscilloscope. This flat or discontinuity 156 is, therefore, reliably indicative of the maximum lung pressure.

The method of the invention, as will be understood from the foregoing description, involves sensing system pressure in the manner described, preferably throughout both the inspiration and expiration phases of each cycle and, in any event, during the initial and terminal portions of inspiration. The sensed pressure is displayed on the oscilloscope and scanned to detect the first and second discontinuities 154 and 156, which are reliably indicative of residual lung pressure and maximum lung pressure, respectively. These readings provide the medical personnel valuable information for use in administering to the patient.

I claim:

1. A method of determining lung pressure during the breathing cycle of a patient undergoing positive pressure breathing therapy by means of a respiration system, comprising the steps of:

sensing pressure at a location in the positive pressure respiration system having a low volume spatial separation, within the fluid communication path between the system and the lungs, from the patient's lungs;

controlling the respiration system to provide a breathing cycle having an inspiration phase, followed by a plateau phase during which expiration is prevented and the sensed pressure falls to the maximum lung pressure, and an expiration phase;

generating and displaying a system pressure versus time characteristic from the sensed pressure; and determining from said characteristic, lung pressure in the patient.

2. A method as set forth in claim 1 wherein said step of determining lung pressure includes:

scanning said pressure versus time characteristic to locate a first discontinuity indicative of residual lung pressure, said first discontinuity being characterized by an abrupt transition in the rate of change of system pressure versus time, from a relatively large positive rate of change to a substantially zero rate of change; and measuring the residual lung pressure as the pressure ordinate of said first discontinuity.

3. A method as set forth in claim 1 wherein said step of determining lung pressure includes:

scanning said pressure versus time characteristic to locate a second discontinuity indicative of maximum lung pressure, said second discontinuity being characterized by an abrupt transition from a minimal rate of change in system pressure versus time to a relatively large negative rate of change; and measuring the maximum lung pressure as the pressure ordinate of said second discontinuity.

4. A method as set forth in claim 1 wherein said step of determining lung pressure from said characteristic includes:

scanning said curve to locate first and second discontinuities indicative of minimum and maximum lung pressure, respectively, said first discontinuity being characterized by an abrupt transition in the rate of change of system pressure versus time, from a relatively large positive rate of change to a substantially zero rate of change, and said second discontinuity being characterized by an abrupt transition from a minimal rate of change in system pressure versus time to a relatively large negative rate of change; and measuring the minimum and maximum lung pressures as the pressure ordinates of said first and second discontinuities, respectively.

* * * * *